(12) United States Patent
Bonaldo

(10) Patent No.: US 6,364,869 B1
(45) Date of Patent: Apr. 2, 2002

(54) MEDICAL CONNECTOR WITH SWABBABLE STOPPER

(75) Inventor: Jean M. Bonaldo, Upland, CA (US)

(73) Assignee: Creative Plastics Technology, LLC, Upland, CA (US)

( * ) Notice: Subject to any disclaimer, the term of this patent is extended or adjusted under 35 U.S.C. 154(b) by 0 days.

(21) Appl. No.: 09/590,309

(22) Filed: Jun. 7, 2000

(51) Int. Cl.[7] .................. A61M 25/16; A61M 5/178
(52) U.S. Cl. .............. 604/537; 604/167.04; 604/167.05
(58) Field of Search .................. 604/533, 523, 604/534–537, 539, 30, 32, 167.01, 167.04, 167.05; 128/912

(56) References Cited

U.S. PATENT DOCUMENTS

| | | | | |
|---|---|---|---|---|
| 3,626,980 A | * | 12/1971 | Svensson | 137/614.2 |
| 3,794,042 A | * | 2/1974 | De Klotz et al. | 128/349 R |
| 5,045,068 A | * | 9/1991 | Kawai et al. | 604/246 |
| 5,195,980 A | * | 3/1993 | Catlin | 604/167 |
| 5,273,533 A | * | 12/1993 | Bonaldo | 604/83 |
| 5,306,243 A | * | 4/1994 | Bonaldo | 604/86 |
| 5,520,666 A | * | 5/1996 | Choudhury et al. | 604/283 |
| 5,669,891 A | * | 9/1997 | Vaillancourt | 604/283 |
| 5,836,924 A | * | 11/1998 | Kelliher et al. | 604/248 |
| 5,947,954 A | * | 9/1999 | Bonaldo | 604/246 |
| 5,950,986 A | * | 9/1999 | Daugherty et al. | 251/149.6 |

* cited by examiner

Primary Examiner—Sharon Kennedy
(74) Attorney, Agent, or Firm—Roth & Goldman, P.A.

(57) ABSTRACT

A medical fluid flowline connector comprised of axially aligned relatively rotatable parts preferably comprising a male Luer and a female Luer and an axially compressed elastomeric valve element therebetween includes an elastomeric swabbable stopper permanently positioned in the female Luer, the stopper having a head urged by spring force outwardly of the female Luer when the spring is compressed and also being retained therein by the spring. The spring may comprise an axially compressible resilient portion of the stopper or it may comprise a separate compressible element. An axially extending elongated post integral with the female Luer is configured with axially extending lobes which define flow passageways and has an end which contacts a deformable slit in a head on the stopper to ensure deformation and opening of the slit as a male Luer at the end of a fluid flowline is inserted against the stopper and displaces and deforms the stopper into the female Luer of the flowline connector during flowline connection. The exposed undeformed outer end of the stopper presents a substantially smooth surface which may be swabbed with alcohol and which prevents ingress of contaminants into the female Luer of the connector.

18 Claims, 3 Drawing Sheets

MEDICAL CONNECTOR WITH SWABBABLE STOPPER

CROSS REFERENCE TO RELATED APPLICATIONS, IF ANY

None

BACKGROUND OF THE INVENTION AND PRIOR ART

The present invention relates to medical connectors for blood transfer, intravenous fluid supply, medication dosage and the like.

My prior U.S. Pat. Nos. 5,273,533 issued Dec. 28, 1993 and U.S. Pat. No. 5,306,243 issued Apr. 26, 1994 each disclose a medical connector valve which employs an elastomeric valve element in the form of an elastomeric septum or fluid barrier disposed in a two part plastic housing. The septum is pierced by an upstream pointed cannula to make the fluid connection. Disconnection of the flow line allows the elastomer to re-seal the connector. Valve opening and closing is regulated by rotating a fluid line connection with respect to a housing in which the cannula and septum are mounted. Such connectors are relatively expensive due to the presence of a cannula and the mounting thereof and are increasingly more likely to leak or become contaminated with particulate material of the septum due to repeated use. Current Food and Drug Administration (FDA) requirements dictate that medical flowline connectors not remain connected for more than 24 hours at a time. For this reason, disconnection of the flowlines and decontamination of the connector and flowlines, as by swabbing with alcohol, is at least a daily occurrence. Thus, these connectors may be actuated or cycled many times and must remain leak free and reliably avoid introduction of contaminants such as cotton fibers from swabs used to clean the connectors into the flowline.

Medical connectors which use resilient flow barriers which are repeatedly pierced during use of the connector become more subject to fluid leakage with increased actuation cycles, particularly if connected in an infusion pump line which may subject the connector to pressures as high as 27 psi. My prior U.S. Pat. No. 5,947,954 issued Sept. 7, 1999, the teachings of which are incorporated herein by reference, discloses a needleless connector which is addressed to the above concerns and which includes relatively rotatable male and female Luer connectors with an eccentricly positioned flow passageway at the inner end of the female Luer connector. A removable plastic plug, permanently attached to the connector by a strap, and which fulfills the function of a cleansing swab for the female Luer connector is also optionally provided as disclosed in my prior patent.

Although the removable plug when properly used closes the female Luer when the female Luer is not connected to a flowline, it has been found in practice that additional manipulation of the plug is required for proper use and that the plug can inadvertently become dislodged leaving the female Luer open to atmosphere and possible contamination. Accordingly, a more reliable and easy to use stopper for the female Luer part of the connector which will always remain in proper position yet which will permit connection/disconnection of the male Luer end of a flowline to/from the connector valve without extra motion or steps is desired. Preferably such a stopper should have an exterior surface which essentially completely closes the otherwise open end of the female Luer, the surface being swabbable without introducing fibers or other contaminants interiorly of the stopper into the female Luer.

OBJECTS OF THE INVENTION

It is the primary objective of the present invention to provide a medical connector which includes an otherwise open female Luer end which is closed with a swabbable elastomeric stopper when the female Luer is not connected to a flowline and which is longitudinally slidable in and which remains in the female Luer part of the connector regardless of whether a flowline is connected thereto.

SUMMARY OF THE INVENTION

The present invention accordingly provides a needle-less medical connector having a longitudinal axis and interconnected relatively rotatable parts aligned on said axis whereby relative rotation of said parts opens and closes a fluid flow path through said connector, at least one of said parts comprising a female Luer, said connector further including an elastomeric stopper having an exterior end surface and a flow passageway extending therethrough, said stopper being slidably fitted into said female Luer for axial movement of said stopper with respect to said female Luer and a spring engaged with said stopper and with said female Luer for retaining said stopper in said female Luer and urging said stopper outwardly of said female Luer when said spring is compressed, said spring having an uncompressed length such that said exterior end surface of said stopper is proximate an end of said female Luer.

The present invention further provides a needle-less medical connector having a longitudinal axis and interconnected relatively rotatable parts aligned on said axis whereby relative rotation of said parts opens and closes a fluid flow path through said connector, at least one of said parts comprising a female Luer, said connector further including an elastomeric stopper having an exterior end surface and a flow passageway extending therethrough, said stopper being slidably fitted into said female Luer for axial movement of at least a portion of said stopper with respect to said female Luer, said elastomeric stopper having an integrally formed resilient skirt affixed to said female Luer, said resilient skirt being axially compressible in said female Luer when engaged by a male Luer end of a fluid flowline to urge said end surface outwardly of said female Luer, said stopper having an uncompressed length such that said exterior end surface is proximate an end of said female Luer.

DESCRIPTION OF THE PREFERRED EMBODIMENT

Figure 1:
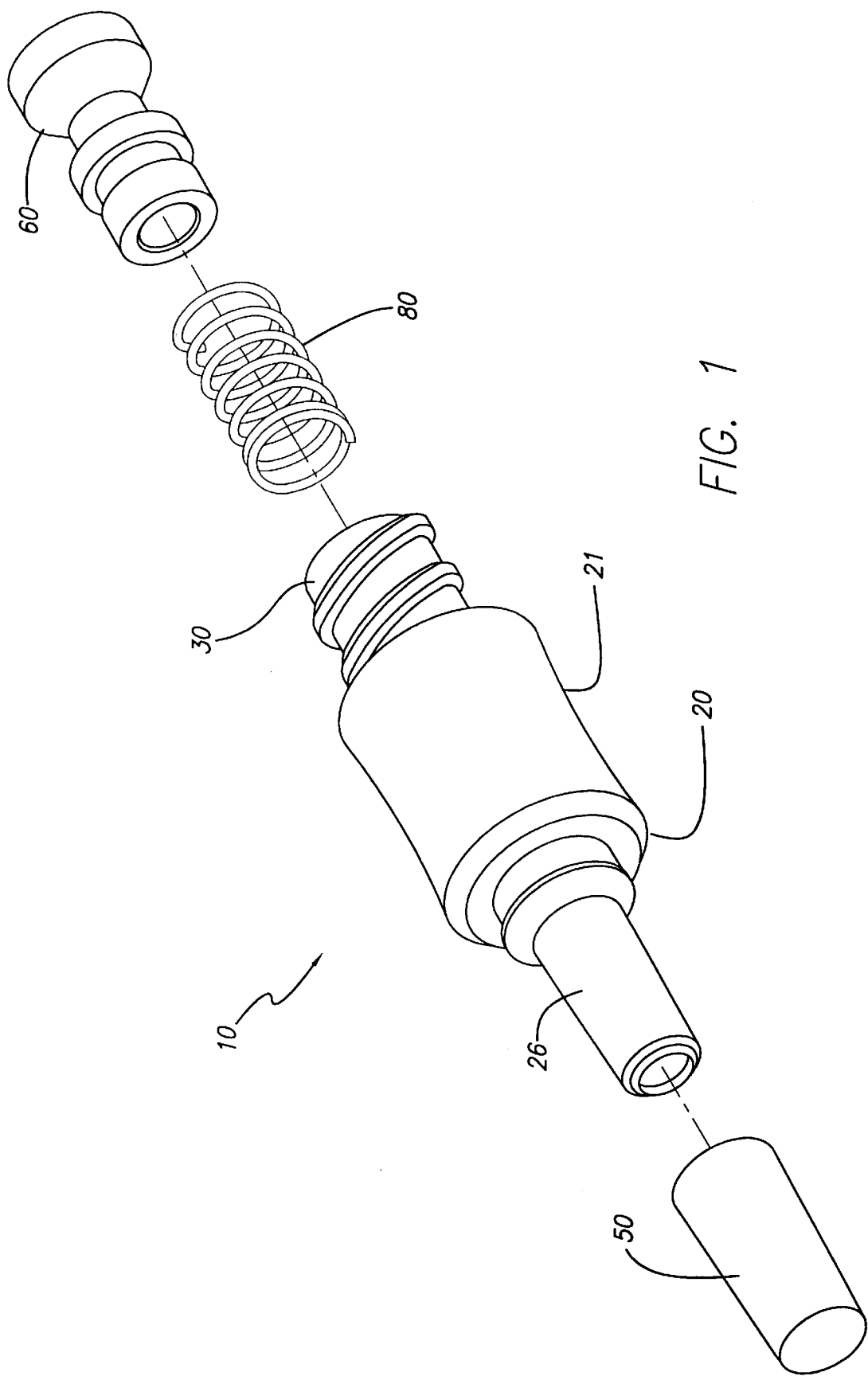
FIG. 1 comprises an exploded perspective view of a first embodiment of a medical connector according to the present invention including a contamination cap for a male Luer part and a swabbable stopper for a female Luer part of the connector.

The medical connector 10 in which the present invention is used comprises essentially a three part connector comprising a valve housing 20 having a male Luer configured part 26 and a female Luer configured part 30 with a resilient valve element 40 which is compressed between a valve seat 22 formed at the end wall in the housing 20 and an end wall 32 of the female Luer part 30. The male Luer housing 20 and female Luer part 30 are aligned on a common longitudinal axis and are rotatable with respect to each other about the longitudinal axis to open and close the valve. A concave gripping surface 21 on the housing 20 facilitates fingertip operation of the connector. As seen in FIG. 1, the male Luer part 26 is configured as a slip Luer and the female Luer part 30 is configured as an externally threaded lock Luer; however, the configuration of the Luer parts 26, 30 is not critical to the present invention and either or both of the Luer parts 26, 30 can be configured as desired as a slip Luer part or as a threaded lock Luer part.

The valve housing 20 has a fluid flow passage 24 therein which extends longitudinally from the male Luer fluid line connection part 26 to the valve seat 22. Similarly, the female Luer part 30 has an axially extending female Luer fluid flow passage 34 therein which, in the embodiment shown, terminates in an off-center positioned flow passage 36 extending through the end wall 32 of the female Luer part 30 which compressively engages the valve element 40.

The valve element 40 has a fluid flow passageway 44 extending therethrough from an axially aligned opening in fluid communication with passage 24 to an off-center positioned end 48 which can be placed into or out of flow communication with off-center actuator passage 36. Valve element 40 is made of a firm but compressible elastomer which is compressed between the valve seat 22 in the housing and the end wall 32 of the actuator during assembly of the valve.

A male end Luer contamination cap 50 may optionally be provided for sealing the male Luer end of the medical connector during shipment or otherwise.

Pursuant to the invention a swabbable elastomeric stopper 60 having an axially extending flow passageway 62 and a normally closed end 64 is slidably mounted in the female Luer part 30 to normally close the open end thereof. A transversely extending slit 66 is provided through the normally closed end 64 of the elastomeric stopper 60 so that the slit can be opened by contact with a male Luer end 102 of a Luer lock 100 when a Bowline connection is made to the connector. It will be understood that the slit 66 may be a single transversely extending slit or two or more slits in form of a cross or any other suitable configuration such that the normally closed end 64 of the stopper 60 will be displaced as desired by the male Luer end 102 when a flowline connection is made.

The stopper 60 shown in FIGS. 1–5 is configured with an annular collar 68 which slidably engages the interior annular wall of the passageway 34 in the female Luer part 30. In this embodiment an annular spring retainer groove 70 is also provided on the stopper 60 into which one or more coils of a compression spring 80 are received. The compression spring 80 is seated and retained in the female Luer part by an interference fit between the inner wall of the passageway 34 and a plurality of axially extending spring retainer fingers 82 integrally formed with the female Luer part 30 at the interior end thereof.

Figure 3:
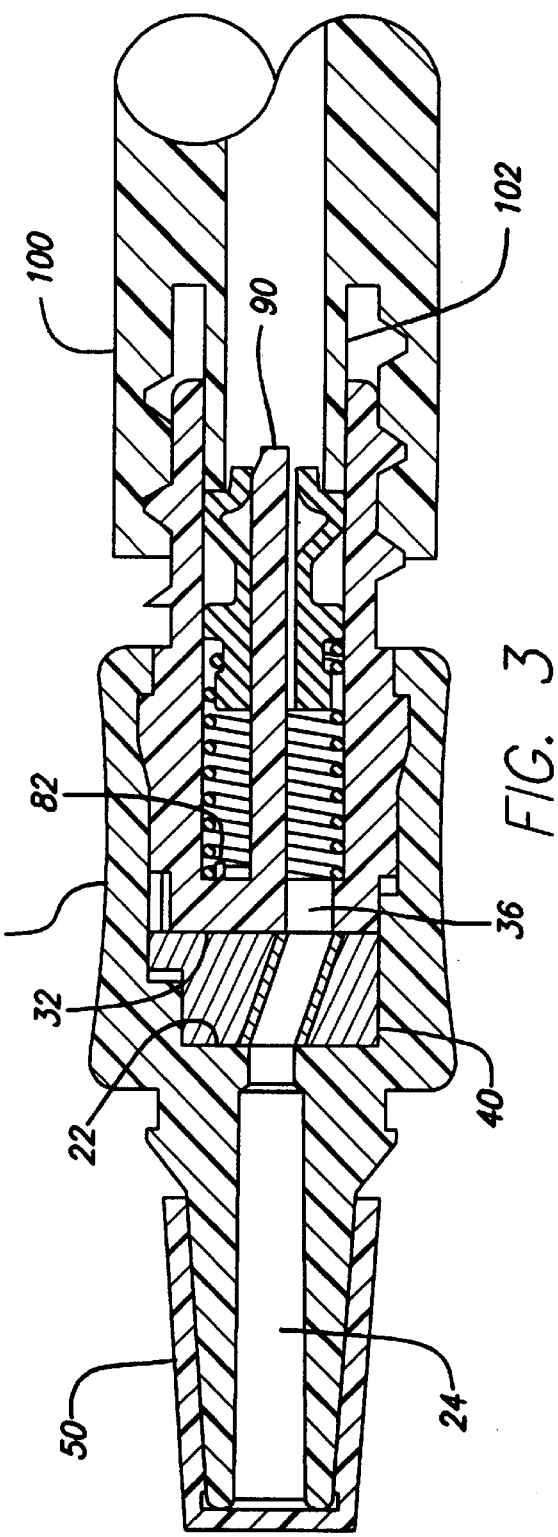
FIG. 3 is a view like FIG. 2 with the swabbable stopper displaced from the FIG. 2 position by a male Luer in a flowline and showing the connector in the valve open position.
Figure 5:
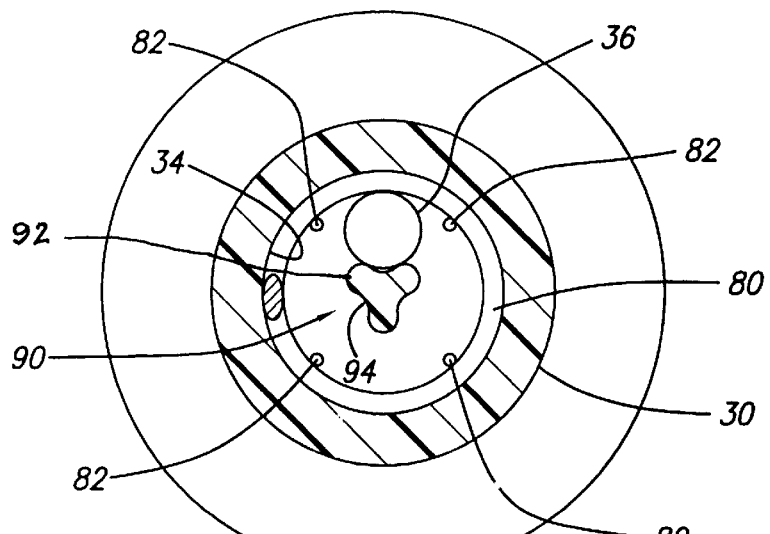
FIG. 5 is a cross section taken at lines 5—5 on FIG. 2.

Also formed integrally with the female Luer part 30 is an axially extending guide post 90 having a plurality of axially extending lobes 92 (three are shown in FIG. 5) which define axially extending flow channels 94 therebetween when the connector is in the open position as shown in FIG. 3. The flow channel through the connector extends from the fluid flowline at the Luer lock 100 through the slit or slits 66 which are displaced to the open position by engagement of the normally closed end wall 64 of the stopper 60 with the male Luer 102 which displaces the stopper 60 to the left as shown in FIG. 3 so that the end of the guide post 90 projects through the slit or slits 66 allowing fluid flow axially through the flow channels 94 and through the interior of the spring 80 to the off-center actuator passage 36, through the passageway 44 in the elastomeric valve element 40 to the passageway 24 in the male Luer part.

Figure 2:
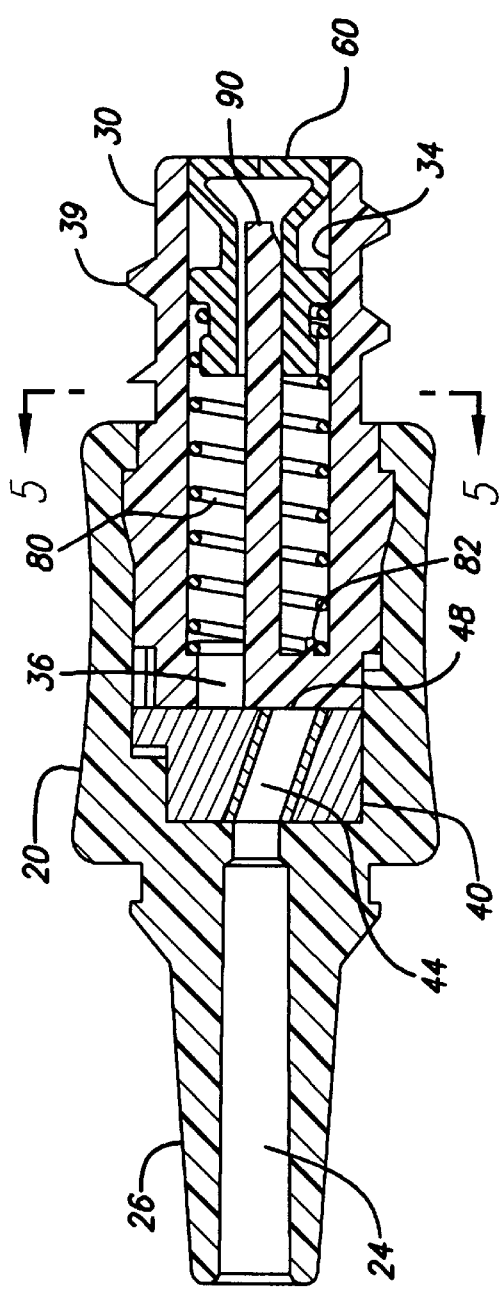
FIG. 2 comprises a longitudinal cross section view showing the medical connector of FIG. 1 with the swabbable stopper closing the end of the female Luer part and with the valve element in the valve closed position.

The length and compression of the spring 80 is selected such that, in the closed position of the connector seen in FIG. 2, the spring urges the stopper 60 outwardly of the internal passageway 34 in the female Luer part 30 so that the normally closed end 64 of the stopper 60 is substantially aligned with the terminal end of the female Luer part 30. This permits easy swabbing of the stopper whenever the flowline is disconnected from the connector and prior to the making of a new connection thereto. The elastomeric stopper 60 permanently remains in the flow passageway 34 and is retained therein by the spring due to engagement of the spring with the spring retainer groove 70 on the stopper 60, the other end of the spring being firmly retained between the interior wall of the passageway 34 and the axially extending spring retainer fingers 82. Reference to FIG. 5 will also show that the off-center flow passage 36 through the end wall 32 of the female Luer part 30 is aligned with one of the flow channels 94 which extend between the lobes 92 of the guide post 90.

Figure 4:
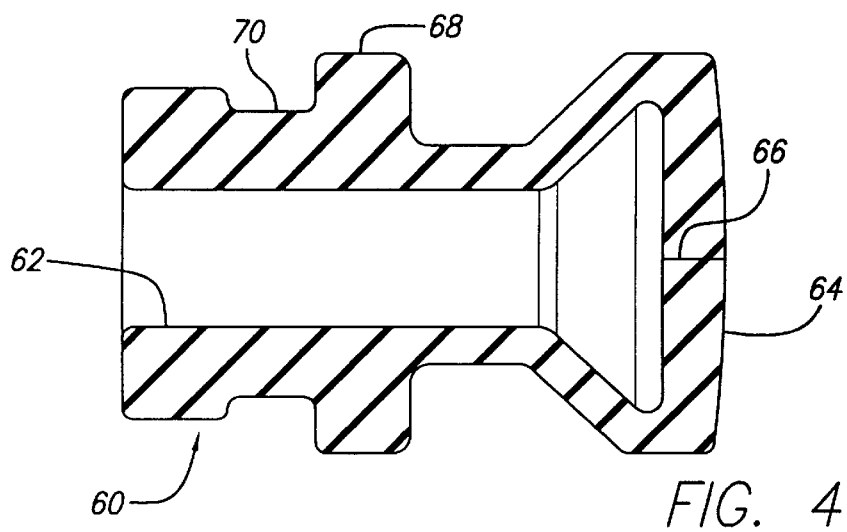
FIG. 4 is a plan cross-section view of the swabbable stopper used in the embodiment of FIG. 1 to an enlarged scale.
Figure 6:
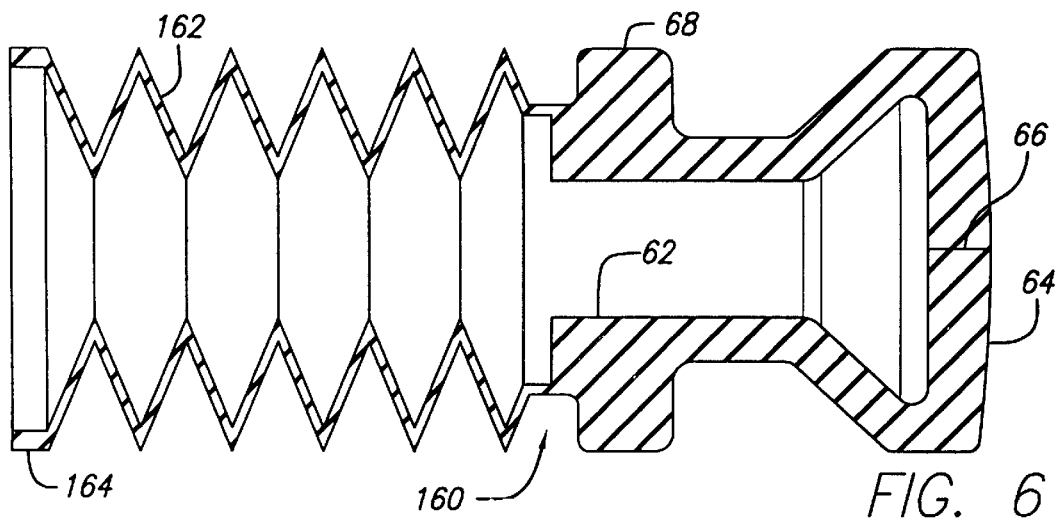
FIG. 6 is a cross section plan view of a second embodiment of swabbable stopper.

FIG. 6 shows a second embodiment of swabbable elastomeric stopper 160 which is configured similar to the embodiment best seen in FIG. 4. Like reference numerals are used to designate like parts in the two different embodiments. The embodiment of FIG. 6 has an elongated skirt 162 through which the passageway 62 extends, the skirt 162 having an accordion like configuration which functions as a resilient spring so that a separate spring 80 as used in the embodiment of the invention shown in FIGS. 1–5 is no longer required. Unlike the swabbable stopper 60 of FIG. 4, the combined length of the spring skirt stopper 160 of the embodiment of FIG. 6 is designed such that the exposed slitted end 64 of the stopper is essentially flush with the end of the female Luer in which it is received and the inner end of the skirt 162 is seated in the inner end of the female Luer 30. The stopper 160 can be permanently retained in the female Luer in any suitable fashion, for example by adhesive or by use of a separate rigid plastic retainer ring 164 adhesively bonded to the inner end of the stopper so that the stopper 160 and attached ring 164 may be press fit into the female Luer part 30 and retained therein by an interference fit due to slight deformation of the ring 164. When the resilient skirt stopper 160 of FIG. 6 is used, the integrally formed spring retaining collar 70 shown on the FIG. 4 stopper 60 and the projections 82 in the female Luer seat which serve to retain the separate spring 80 shown in the embodiment of FIGS. 1–5 are not required. Such projections can, of course also be used to retain the ring 164 in the same fashion that they are used to retain the spring 80.

While the foregoing constitutes a complete description of the invention, it will be appreciated by persons skilled in the art that modifications can be made from the illustrated embodiments and that the scope of protection is to be evaluated solely with respect to the attached claims.

What is claimed is:

1. A medical connector having a longitudinal axis and interconnected relatively rotatable parts aligned on said axis whereby relative rotation of said parts opens and closes a fluid flow path through said connector, at least one of said parts comprising a female Luer including an integrally formed post therein extending axially outwardly from an inner end surface of said female Luer, said connector further including an elastomeric stopper having an exterior end surface and a flow passageway extending through said end surface capable of deforming upon contact with said post to open said flow passageway to permit fluid flow axially along said post through said passageway, said stopper being slidably fitted into said female Luer for axial movement of said stopper with respect to said female Luer and a spring engaged with said stopper and with said female Luer for retaining said stopper in said female Luer and urging said stopper outwardly of said female Luer when said spring is compressed, said spring having an uncompressed length such that said exterior end surface of said stopper is proximate an end of said female Luer.

2. The medical connector of claim 1, wherein said stopper comprises a tubular skirt and said exterior end surface is on a head closing one end of said skirt, said deformable flow passageway comprising a slit, said head being deformable when said head is contacted by a male Luer part to place a flow passage in said male Luer part into fluid communication with said connector fluid flow path.

3. The medical connector of claim 2, wherein said stopper has a generally circular cross section and a first portion of said spring is engaged with a seat in said female Luer part for retaining said spring in said female Luer part and a second end portion of said spring is affixed to said skirt.

4. The medical connector of claim 3, wherein said spring is a coil compression spring and has an end coil received in a spring retainer on said skirt.

5. The medical connector of claim 4, wherein said spring retainer is an annular groove on an exterior surface of said skirt.

6. The medical connector of claim 5, wherein said seat in said female Luer part is configured to retain said first end portion of said spring between a concave wall of said female Luer part and integrally formed generally axially extending projections in said female Luer part.

7. The medical connector of claim 1, wherein said post has a transverse cross sectional area less than the transverse cross sectional area of the inside of said skirt to provide said fluid flow path between said post and said skirt.

8. The medical connector of claim 7, wherein said post has an end located inwardly of said head at a location to be contacted by said head during movement of said stopper inwardly of said female Luer part whereby said deformable portion in said head is deformed by said post as said stopper is moved further axially inwardly into said female Luer part.

9. The medical connector of claim 8, wherein said post has a non-circular cross-section.

10. The medical connector of claim 9, wherein said cross-section of said post comprises a plurality of lobes.

11. The medical connector of claim 8, wherein said stopper is silicone elastomer.

12. A medical connector having a longitudinal axis and interconnected relatively rotatable parts aligned on said axis whereby relative rotation of said parts opens and closes a fluid flow path through said connector, at least one of said parts comprising a female Luer including an integrally formed post therein extending axially outwardly from an inner end surface of said female Luer, said connector further including an elastomeric stopper having an exterior end surface and a flow passageway extending through said end surface capable of deforming upon contact with said post to open said flow passageway to permit fluid flow therethrough in an axial direction alongside said post, said stopper being slidably fitted into said female Luer for axial movement of at least a portion of said stopper with respect to said female Luer, said elastomeric stopper having an integrally formed resilient skirt affixed to said female Luer, said resilient skirt being axially compressible in said female Luer when engaged by a male Luer end of a fluid flowline to urge said end surface outwardly of said female Luer, said stopper having an uncompressed length such that said exterior end surface is proximate an end of said female Luer.

13. The medical connector of claim 12, wherein said end surface is on a head closing one end of said skirt, said deformable flow passageway comprising a slit, said head and said slit being deformable when contacted by a male Luer part to place a flow passage in said male Luer part into fluid communication with said connector fluid flow path.

14. The medical connector of claim 13, wherein said skirt is of accordion configuration.

15. The medical connector of claim 14, wherein an end portion of said skirt is adhesively bonded to a seat at an inner end of said female Luer.

16. The medical connector of claim 13, further comprising an end ring adhesively bonded to an end of said skirt and wherein said end ring engages said female Luer to retain said stopper in said female Luer.

17. The medical connector of claim 12, wherein said post has a transverse cross sectional area less than the transverse cross sectional area of the inside of said skirt to provide said fluid flow path between said post and said skirt.

18. The medical connector of claim 17, wherein said post has an end located inwardly of said head at a location to be contacted by said head during movement of said head inwardly of said female Luer part whereby said slit in said head is deformed by said post as said stopper is moved further axially inwardly into said female Luer part.

* * * * *